United States Patent
Rusin et al.

(10) Patent No.: US 9,949,794 B2
(45) Date of Patent: Apr. 24, 2018

(54) MICROWAVE ABLATION DEVICES INCLUDING EXPANDABLE ANTENNAS AND METHODS OF USE

(75) Inventors: Christopher T. Rusin, Minneapolis, MN (US); Darion Peterson, Boulder, CO (US); Tao D. Nguyen, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 1141 days.

(21) Appl. No.: 12/413,011

(22) Filed: Mar. 27, 2009

(65) Prior Publication Data

US 2009/0248005 A1  Oct. 1, 2009

Related U.S. Application Data

(60) Provisional application No. 61/039,851, filed on Mar. 27, 2008.

(51) Int. Cl.
  *A61B 18/18* (2006.01)
  *A61N 5/02* (2006.01)
  *A61B 18/00* (2006.01)

(52) U.S. Cl.
  CPC .......... *A61B 18/18* (2013.01); *A61B 18/1815* (2013.01); *A61N 5/02* (2013.01);
  (Continued)

(58) Field of Classification Search
  CPC ................ A61B 18/18; A61B 18/1815; A61B 2018/00214–2018/00267; A61N 5/02;
  (Continued)

(56) References Cited

U.S. PATENT DOCUMENTS 3,631,363 A   12/1971 Miller
D223,367 S    4/1972 Kountz
              (Continued)

FOREIGN PATENT DOCUMENTS

CN    1103807 A    6/1995
CN    101553181 A  10/2009
                   (Continued)

OTHER PUBLICATIONS

U.S. Appl. No. 08/483,742, filed Jun. 7, 1995.
(Continued)

*Primary Examiner* — Bhisma Mehta
*Assistant Examiner* — Larry R Wilson

(57) ABSTRACT

A microwave ablation device for treating tissue includes an inner conductor having a length and a distal end and configured to deliver energy, a wire extending adjacent the inner conductor and axially translatable relative thereto, the wire including a length and a distal end, a distal tip disposed in mechanical cooperation with the distal end of the inner conductor and the distal end of the wire; and an outer conductor including a distal end and defining a longitudinal axis, the outer conductor at least partially surrounding the inner conductor and the wire at least partially along their lengths. The distal tip is movable substantially along the longitudinal axis with respect to the outer conductor and relative movement of the distal tip towards the distal end of the outer conductor causes at least a portion of the inner conductor to move away from the longitudinal axis.

14 Claims, 5 Drawing Sheets

(52) U.S. Cl.
CPC .............. *A61B 2018/00214* (2013.01); *A61B 2018/00267* (2013.01)

(58) Field of Classification Search
CPC .......... A61N 5/022; A61N 5/025; A61N 5/04; A61N 5/045; A61N 2005/027
USPC ............ 606/33, 34, 37–39, 41; 604/10–109; 607/101–105, 154–156
See application file for complete search history.

(56) References Cited

U.S. PATENT DOCUMENTS

| | | | |
|---|---|---|---|
| D263,020 S | 2/1982 | Rau, III | |
| D266,842 S | 11/1982 | Villers et al. | |
| 4,397,313 A | 8/1983 | Vaguine | |
| 4,462,412 A | 7/1984 | Turner | |
| D278,306 S | 4/1985 | McIntosh | |
| 4,572,190 A | 2/1986 | Azam et al. | |
| 4,643,186 A | 2/1987 | Rosen et al. | |
| D295,893 S | 5/1988 | Sharkany et al. | |
| D295,894 S | 5/1988 | Sharkany et al. | |
| 4,798,215 A | 1/1989 | Turner | |
| 5,057,106 A * | 10/1991 | Kasevich et al. | 606/33 |
| 5,097,844 A | 3/1992 | Turner | |
| 5,248,312 A | 9/1993 | Langberg | |
| 5,257,635 A | 11/1993 | Langberg | |
| 5,275,597 A | 1/1994 | Higgins et al. | |
| 5,281,217 A | 1/1994 | Edwards et al. | |
| 5,364,392 A | 11/1994 | Warner et al. | |
| 5,366,490 A | 11/1994 | Edwards et al. | |
| 5,370,675 A | 12/1994 | Edwards et al. | |
| D354,218 S | 1/1995 | Van de Peer | |
| 5,405,346 A | 4/1995 | Grundy et al. | |
| 5,417,210 A | 5/1995 | Funda et al. | |
| 5,470,308 A | 11/1995 | Edwards et al. | |
| 5,472,441 A | 12/1995 | Edwards et al. | |
| 5,507,743 A | 4/1996 | Edwards et al. | |
| 5,536,240 A | 7/1996 | Edwards et al. | |
| 5,536,267 A | 7/1996 | Edwards et al. | |
| 5,556,377 A | 9/1996 | Rosen et al. | |
| 5,558,673 A | 9/1996 | Edwards et al. | |
| 5,562,720 A | 10/1996 | Stern et al. | |
| 5,571,147 A | 11/1996 | Sluijter et al. | |
| 5,599,294 A | 2/1997 | Edwards et al. | |
| 5,599,295 A | 2/1997 | Rosen et al. | |
| 5,607,389 A | 3/1997 | Edwards et al. | |
| 5,693,082 A | 12/1997 | Warner et al. | |
| 5,720,718 A | 2/1998 | Rosen et al. | |
| 5,722,401 A | 3/1998 | Pietroski et al. | |
| 5,776,176 A | 7/1998 | Rudie | |
| 5,800,484 A | 9/1998 | Gough et al. | |
| 5,800,486 A | 9/1998 | Thome et al. | |
| 5,800,494 A | 9/1998 | Campbell et al. | |
| 5,846,238 A * | 12/1998 | Jackson | A61B 18/1492 600/374 |
| 5,861,021 A | 1/1999 | Thome et al. | |
| 5,863,290 A | 1/1999 | Gough et al. | |
| 5,871,525 A | 2/1999 | Edwards et al. | |
| 5,902,251 A | 5/1999 | vanHooydonk | |
| 5,921,982 A | 7/1999 | Lesh et al. | |
| 5,951,547 A | 9/1999 | Gough et al. | |
| 5,957,969 A | 9/1999 | Warner et al. | |
| 5,964,755 A | 10/1999 | Edwards | |
| 6,016,452 A | 1/2000 | Kasevich | |
| 6,024,740 A | 2/2000 | Lesh et al. | |
| 6,031,375 A | 2/2000 | Atalar et al. | |
| 6,047,216 A | 4/2000 | Carl et al. | |
| 6,052,607 A | 4/2000 | Edwards et al. | |
| D424,693 S | 5/2000 | Pruter | |
| D424,694 S | 5/2000 | Tetzlaff et al. | |
| D425,201 S | 5/2000 | Tetzlaff et al. | |
| 6,056,744 A | 5/2000 | Edwards | |
| 6,117,101 A | 9/2000 | Diederich et al. | |
| 6,210,367 B1 * | 4/2001 | Carr | A61B 18/18 604/114 |
| 6,223,086 B1 | 4/2001 | Carl et al. | |
| 6,226,553 B1 | 5/2001 | Carl et al. | |
| 6,245,064 B1 | 6/2001 | Lesh et al. | |
| 6,246,912 B1 | 6/2001 | Sluijter et al. | |
| 6,290,715 B1 | 9/2001 | Sharkey et al. | |
| D449,886 S | 10/2001 | Tetzlaff et al. | |
| 6,306,132 B1 | 10/2001 | Moorman et al. | |
| 6,350,276 B1 | 2/2002 | Knowlton | |
| 6,355,033 B1 | 3/2002 | Moorman et al. | |
| 6,375,606 B1 | 4/2002 | Garibaldi et al. | |
| D457,958 S | 5/2002 | Dycus et al. | |
| D457,959 S | 5/2002 | Tetzlaff et al. | |
| 6,413,255 B1 | 7/2002 | Stern | |
| 6,419,653 B2 | 7/2002 | Edwards et al. | |
| 6,425,912 B1 | 7/2002 | Knowlton | |
| 6,430,446 B1 | 8/2002 | Knowlton | |
| 6,451,015 B1 | 9/2002 | Rittman, III et al. | |
| 6,477,426 B1 | 11/2002 | Fenn et al. | |
| 6,496,736 B1 | 12/2002 | Carl et al. | |
| 6,496,738 B2 | 12/2002 | Carr | |
| 6,514,249 B1 | 2/2003 | Maguire et al. | |
| 6,526,320 B2 | 2/2003 | Mitchell | |
| 6,547,788 B1 | 4/2003 | Maguire et al. | |
| 6,551,311 B2 | 4/2003 | Lee et al. | |
| 6,569,159 B1 | 5/2003 | Edwards et al. | |
| 6,582,426 B2 | 6/2003 | Moorman et al. | |
| 6,599,288 B2 | 7/2003 | Maguire et al. | |
| 6,603,994 B2 | 8/2003 | Wallace et al. | |
| 6,610,054 B1 | 8/2003 | Edwards et al. | |
| 6,622,731 B2 | 9/2003 | Daniel et al. | |
| 6,652,515 B1 | 11/2003 | Maguire et al. | |
| 6,652,520 B2 | 11/2003 | Moorman et al. | |
| 6,673,070 B2 | 1/2004 | Edwards et al. | |
| D487,039 S | 2/2004 | Webster et al. | |
| 6,725,080 B2 | 4/2004 | Melkent et al. | |
| 6,788,977 B2 | 9/2004 | Fenn et al. | |
| D496,997 S | 10/2004 | Dycus et al. | |
| D499,181 S | 11/2004 | Dycus et al. | |
| 6,847,848 B2 | 1/2005 | Sterzer et al. | |
| 6,852,091 B2 | 2/2005 | Edwards et al. | |
| 6,869,431 B2 | 3/2005 | Maguire et al. | |
| 6,878,147 B2 | 4/2005 | Prakash et al. | |
| 6,932,776 B2 | 8/2005 | Carr | |
| 6,997,925 B2 | 2/2006 | Maguire et al. | |
| D525,361 S | 7/2006 | Hushka | |
| 7,089,063 B2 | 8/2006 | Lesh et al. | |
| D531,311 S | 10/2006 | Guerra et al. | |
| 7,118,590 B1 | 10/2006 | Cronin | |
| 7,128,739 B2 | 10/2006 | Prakash et al. | |
| D533,942 S | 12/2006 | Kerr et al. | |
| 7,147,632 B2 | 12/2006 | Prakash et al. | |
| D535,027 S | 1/2007 | James et al. | |
| 7,160,292 B2 | 1/2007 | Moorman et al. | |
| 7,160,296 B2 | 1/2007 | Pearson et al. | |
| 7,160,299 B2 | 1/2007 | Baily | |
| 7,186,251 B2 | 3/2007 | Malecki et al. | |
| D541,418 S | 4/2007 | Schechter et al. | |
| D541,938 S | 5/2007 | Kerr et al. | |
| 7,252,665 B2 | 8/2007 | Starkebaum et al. | |
| 7,267,683 B2 | 9/2007 | Sharkey et al. | |
| 7,276,061 B2 | 10/2007 | Schaer et al. | |
| 7,278,991 B2 | 10/2007 | Morris et al. | |
| 7,282,050 B2 | 10/2007 | Starkebaum et al. | |
| 7,282,061 B2 | 10/2007 | Sharkey et al. | |
| 7,291,146 B2 | 11/2007 | Steinke et al. | |
| 7,311,703 B2 | 12/2007 | Turovskiy et al. | |
| 7,318,824 B2 | 1/2008 | Prakash et al. | |
| 7,326,201 B2 | 2/2008 | Fjield et al. | |
| D564,662 S | 3/2008 | Moses et al. | |
| 7,344,533 B2 | 3/2008 | Pearson et al. | |
| 7,371,235 B2 | 5/2008 | Thompson et al. | |
| 7,387,626 B2 | 6/2008 | Edwards et al. | |
| 7,399,299 B2 * | 7/2008 | Daniel | A61B 18/148 606/41 |
| D576,932 S | 9/2008 | Strehler | |
| 7,422,586 B2 | 9/2008 | Morris et al. | |
| 7,439,736 B2 | 10/2008 | Meaney et al. | |
| 7,465,300 B2 | 12/2008 | Arless et al. | |
| 7,467,015 B2 | 12/2008 | van der Weide | |

(56) References Cited

U.S. PATENT DOCUMENTS

| | | | |
|---|---|---|---|
| D594,736 S | 6/2009 | Esjunin | |
| D594,737 S | 6/2009 | Kelly et al. | |
| 7,565,207 B2 | 7/2009 | Turner et al. | |
| 7,615,049 B2* | 11/2009 | West et al. | 606/41 |
| D606,203 S | 12/2009 | Husheer et al. | |
| 7,642,451 B2 | 1/2010 | Bonn | |
| D613,412 S | 4/2010 | DeCarlo | |
| 7,875,024 B2 | 1/2011 | Turovskiy et al. | |
| D634,010 S | 3/2011 | DeCarlo | |
| 8,035,570 B2 | 10/2011 | Prakash et al. | |
| 8,059,059 B2 | 11/2011 | Bonn | |
| 8,118,808 B2 | 2/2012 | Smith et al. | |
| 8,182,480 B2 | 5/2012 | Huseman | |
| 8,192,427 B2 | 6/2012 | Buysse | |
| 8,197,473 B2 | 6/2012 | Rossetto et al. | |
| 8,202,270 B2 | 6/2012 | Rossetto et al. | |
| 8,211,098 B2 | 7/2012 | Paulus | |
| 8,211,099 B2 | 7/2012 | Buysse et al. | |
| 8,216,227 B2 | 7/2012 | Podhajsky | |
| 8,221,418 B2 | 7/2012 | Prakash et al. | |
| 8,235,981 B2 | 8/2012 | Prakash et al. | |
| 8,246,614 B2 | 8/2012 | DeCarlo | |
| 8,251,987 B2 | 8/2012 | Willyard | |
| 8,262,703 B2 | 9/2012 | Prakash et al. | |
| 8,292,880 B2 | 10/2012 | Prakash et al. | |
| 8,292,881 B2 | 10/2012 | Brannan et al. | |
| 8,343,149 B2 | 1/2013 | Rossetto et al. | |
| 8,353,902 B2 | 1/2013 | Prakash | |
| 8,353,903 B2 | 1/2013 | Podhajsky | |
| 8,394,086 B2 | 3/2013 | Behnke et al. | |
| 8,435,237 B2 | 5/2013 | Bahney | |
| 8,463,396 B2 | 6/2013 | Podhajsky | |
| 8,512,328 B2 | 8/2013 | Rossetto et al. | |
| 8,834,409 B2 | 9/2014 | Manley | |
| 8,834,460 B2 | 9/2014 | Peterson | |
| 8,945,111 B2 | 2/2015 | Brannan et al. | |
| 8,965,536 B2 | 2/2015 | Bonn et al. | |
| 9,113,924 B2 | 8/2015 | Brannan et al. | |
| 9,113,931 B2 | 8/2015 | Lee et al. | |
| 9,119,648 B2 | 9/2015 | Lee et al. | |
| 9,173,706 B2 | 11/2015 | Rossetto | |
| 9,198,723 B2 | 12/2015 | Paulus et al. | |
| 2002/0022836 A1 | 2/2002 | Goble et al. | |
| 2002/0120261 A1 | 8/2002 | Morris et al. | |
| 2003/0032951 A1 | 2/2003 | Rittman et al. | |
| 2003/0195499 A1 | 10/2003 | Prakash et al. | |
| 2004/0097805 A1 | 5/2004 | Verard et al. | |
| 2004/0242992 A1 | 12/2004 | Hareyama | |
| 2005/0038419 A9 | 2/2005 | Arnold et al. | |
| 2005/0096647 A1 | 5/2005 | Steinke et al. | |
| 2005/0137662 A1 | 6/2005 | Morris et al. | |
| 2005/0149010 A1 | 7/2005 | Turovskiy et al. | |
| 2005/0197570 A1 | 9/2005 | Carr | |
| 2005/0203388 A1 | 9/2005 | Carr | |
| 2005/0228370 A1 | 10/2005 | Sterzer et al. | |
| 2005/0240239 A1 | 10/2005 | Boveja et al. | |
| 2005/0256521 A1* | 11/2005 | Kozel | A61B 5/0422 606/41 |
| 2006/0015162 A1 | 1/2006 | Edward et al. | |
| 2006/0030914 A1 | 2/2006 | Eggers et al. | |
| 2006/0106375 A1 | 5/2006 | Werneth et al. | |
| 2006/0264923 A1 | 11/2006 | Prakash et al. | |
| 2006/0282069 A1 | 12/2006 | Prakash et al. | |
| 2006/0293650 A1 | 12/2006 | Prakash et al. | |
| 2006/0293651 A1 | 12/2006 | Cronin | |
| 2007/0060989 A1 | 3/2007 | Deem et al. | |
| 2007/0156140 A1 | 7/2007 | Baily | |
| 2007/0161977 A1 | 7/2007 | Moorman et al. | |
| 2007/0191825 A1 | 8/2007 | Cronin et al. | |
| 2007/0219546 A1 | 9/2007 | Mody et al. | |
| 2007/0233057 A1 | 10/2007 | Konishi | |
| 2007/0299434 A1 | 12/2007 | Malecki et al. | |
| 2008/0308256 A1 | 12/2008 | Deborski et al. | |
| 2009/0192508 A1* | 7/2009 | Laufer et al. | 606/41 |
| 2009/0248005 A1 | 10/2009 | Rusin et al. | |
| 2009/0306652 A1 | 12/2009 | Buysse et al. | |
| 2010/0030206 A1 | 2/2010 | Brannan et al. | |
| 2010/0030210 A1 | 2/2010 | Paulus | |
| 2010/0045559 A1 | 2/2010 | Rossetto | |
| 2010/0049189 A1 | 2/2010 | Dickens | |
| 2010/0076422 A1 | 3/2010 | Podhajsky | |
| 2010/0087808 A1 | 4/2010 | Paulus | |
| 2010/0094273 A1 | 4/2010 | Rossetto et al. | |
| 2010/0256624 A1 | 10/2010 | Brannan et al. | |
| 2010/0262134 A1 | 10/2010 | Jensen et al. | |
| 2012/0004650 A1 | 1/2012 | Shiu et al. | |
| 2014/0214017 A1 | 7/2014 | Brannan | |
| 2014/0214023 A1 | 7/2014 | Prakash et al. | |
| 2014/0257267 A1 | 9/2014 | Shiu et al. | |
| 2014/0290045 A1 | 10/2014 | Bonn | |
| 2014/0296840 A1 | 10/2014 | Behnke | |
| 2014/0296841 A1 | 10/2014 | Brannan | |
| 2015/0065944 A1 | 3/2015 | Ohri et al. | |
| 2015/0065964 A1 | 3/2015 | Ohri et al. | |
| 2015/0305809 A1 | 10/2015 | Prakash et al. | |

FOREIGN PATENT DOCUMENTS

| | | |
|---|---|---|
| DE | 390937 | 3/1924 |
| DE | 390937 C | 3/1924 |
| DE | 1099658 | 2/1961 |
| DE | 1099658 B | 2/1961 |
| DE | 1139927 | 11/1962 |
| DE | 1139927 B | 11/1962 |
| DE | 1149832 | 6/1963 |
| DE | 1149832 B | 6/1963 |
| DE | 1439302 | 1/1969 |
| DE | 1439302 A1 | 1/1969 |
| DE | 2439587 | 2/1975 |
| DE | 2439587 A1 | 2/1975 |
| DE | 2455174 | 5/1975 |
| DE | 2455174 A1 | 5/1975 |
| DE | 2407559 | 8/1975 |
| DE | 2407559 A1 | 8/1975 |
| DE | 2415263 | 10/1975 |
| DE | 2415263 A1 | 10/1975 |
| DE | 2429021 | 1/1976 |
| DE | 2429021 A1 | 1/1976 |
| DE | 2460481 | 6/1976 |
| DE | 2460481 A1 | 6/1976 |
| DE | 2602517 | 7/1976 |
| DE | 2602517 A1 | 7/1976 |
| DE | 2429021 | 8/1976 |
| DE | 2504280 | 8/1976 |
| DE | 2504280 A1 | 8/1976 |
| DE | 2627679 | 1/1977 |
| DE | 2627679 A1 | 1/1977 |
| DE | 2540968 | 3/1977 |
| DE | 2540968 A1 | 3/1977 |
| DE | 2820908 | 11/1978 |
| DE | 2820908 A1 | 11/1978 |
| DE | 2803275 | 8/1979 |
| DE | 2803275 A1 | 8/1979 |
| DE | 2823291 | 11/1979 |
| DE | 2823291 A1 | 11/1979 |
| DE | 2946728 | 5/1981 |
| DE | 2946728 A1 | 5/1981 |
| DE | 3143421 | 5/1982 |
| DE | 3143421 A1 | 5/1982 |
| DE | 3045996 | 7/1982 |
| DE | 3045996 A1 | 7/1982 |
| DE | 3120102 | 12/1982 |
| DE | 3120102 A1 | 12/1982 |
| DE | 3510586 | 10/1986 |
| DE | 3510586 A1 | 10/1986 |
| DE | 3604823 | 8/1987 |
| DE | 3604823 A1 | 8/1987 |
| DE | 8712328 U1 | 2/1988 |
| DE | 8712328 | 3/1988 |
| DE | 3711511 | 6/1988 |
| DE | 3711511 C1 | 6/1988 |
| DE | 3904558 | 8/1990 |
| DE | 3904558 A1 | 8/1990 |
| DE | 3942998 | 7/1991 |

(56) References Cited

FOREIGN PATENT DOCUMENTS

| | | |
|---|---|---|
| DE | 3942998 A1 | 7/1991 |
| DE | 4238263 | 5/1993 |
| DE | 4238263 A1 | 5/1993 |
| DE | 0556705 | 8/1993 |
| DE | 0558429 | 9/1993 |
| DE | 4303882 | 8/1994 |
| DE | 04303882 C2 | 2/1995 |
| DE | 4339049 | 5/1995 |
| DE | 4339049 A1 | 5/1995 |
| DE | 29616210 U1 | 11/1996 |
| DE | 29616210 | 1/1997 |
| DE | 19608716 | 4/1997 |
| DE | 19608716 C1 | 4/1997 |
| DE | 19751106 | 5/1998 |
| DE | 19751106 A1 | 5/1998 |
| DE | 19717411 | 11/1998 |
| DE | 19717411 A1 | 11/1998 |
| DE | 19751108 | 5/1999 |
| DE | 19751108 A1 | 5/1999 |
| DE | 19801173 | 7/1999 |
| DE | 19801173 C1 | 7/1999 |
| DE | 19848540 | 10/1999 |
| DE | 19848540 | 5/2000 |
| DE | 19848540 A1 | 5/2000 |
| DE | 10224154 | 12/2003 |
| DE | 10224154 A1 | 12/2003 |
| DE | 10310765 A1 | 9/2004 |
| DE | 10328514 | 3/2005 |
| DE | 10328514 B3 | 3/2005 |
| DE | 102004022206 | 12/2005 |
| DE | 102004022206 A1 | 12/2005 |
| DE | 202005015147 U1 | 2/2006 |
| DE | 202005015147 | 3/2006 |
| DE | 1810627 | 7/2007 |
| EP | 0 246 350 | 11/1987 |
| EP | 0 246 350 A1 | 11/1987 |
| EP | 0 481 685 | 4/1992 |
| EP | 0 481 685 A1 | 4/1992 |
| EP | 0 521 264 | 1/1993 |
| EP | 0 521 264 A2 | 1/1993 |
| EP | 0 541 930 | 5/1993 |
| EP | 0541930 A1 | 5/1993 |
| EP | 0 556 705 | 8/1993 |
| EP | 0 556 705 A1 | 8/1993 |
| EP | 0 558 429 | 9/1993 |
| EP | 0 558 429 A1 | 9/1993 |
| EP | 0 572 131 | 12/1993 |
| EP | 0572131 A1 | 12/1993 |
| EP | 0 648 515 A1 | 4/1995 |
| EP | 0 667 126 A1 | 8/1995 |
| EP | 0 836 868 | 4/1998 |
| EP | 0 836 868 A2 | 4/1998 |
| EP | 0 882 955 A1 | 12/1998 |
| EP | 0 667 126 | 3/1999 |
| EP | 0 908 156 | 4/1999 |
| EP | 0908156 A1 | 4/1999 |
| EP | 1 070 518 | 1/2001 |
| EP | 1 070 518 A2 | 1/2001 |
| EP | 1 159 926 | 5/2001 |
| EP | 1 186 274 | 3/2002 |
| EP | 1186274 A2 | 3/2002 |
| EP | 1 278 007 | 1/2003 |
| EP | 1278007 A1 | 1/2003 |
| EP | 1159926 A3 | 3/2003 |
| EP | 1 810 627 A1 | 7/2007 |
| EP | 2937054 A1 | 10/2015 |
| FR | 179 607 | 11/1906 |
| FR | 179607 | 11/1906 |
| FR | 1 275 415 | 9/1960 |
| FR | 1 275 415 A | 11/1961 |
| FR | 1 347 865 | 11/1963 |
| FR | 1 347 865 A | 1/1964 |
| FR | 2 276 027 | 6/1974 |
| FR | 2 235 669 | 1/1975 |
| FR | 2 235 669 A1 | 1/1975 |
| FR | 2 276 027 A1 | 1/1976 |
| FR | 2 313 708 | 12/1976 |
| FR | 2 313 708 A1 | 12/1976 |
| FR | 2 502 935 | 10/1982 |
| FR | 2 502 935 A1 | 10/1982 |
| FR | 2 517 953 | 6/1983 |
| FR | 2 517 953 A1 | 6/1983 |
| FR | 2 573 301 | 11/1984 |
| FR | 2 573 301 A1 | 5/1986 |
| FR | 2 862 813 | 5/2005 |
| FR | 2 862 813 A1 | 5/2005 |
| FR | 2 864 439 | 7/2005 |
| FR | 2 864 439 A1 | 7/2005 |
| GB | 2 388 039 | 11/2003 |
| GB | 2388039 A | 11/2003 |
| JP | 5-5106 | 1/1993 |
| JP | 05-40112 | 2/1993 |
| JP | 06343644 | 12/1994 |
| JP | 06343644 A | 12/1994 |
| JP | 07265328 | 10/1995 |
| JP | 07265328 A | 10/1995 |
| JP | 8-56955 | 3/1996 |
| JP | 08056955 | 3/1996 |
| JP | 08252263 | 10/1996 |
| JP | 08252263 A | 10/1996 |
| JP | 9-10223 | 1/1997 |
| JP | 09000492 A | 1/1997 |
| JP | 09010223 | 1/1997 |
| JP | 11244298 | 9/1999 |
| JP | 11244298 A | 9/1999 |
| JP | 2000342599 | 12/2000 |
| JP | 2000342599 A | 12/2000 |
| JP | 2000350732 | 12/2000 |
| JP | 2000350732 A | 12/2000 |
| JP | 2001003776 A | 1/2001 |
| JP | 2001008944 | 1/2001 |
| JP | 2001008944 A | 1/2001 |
| JP | 2001029356 | 2/2001 |
| JP | 2001029356 A | 2/2001 |
| JP | 2001037775 A | 2/2001 |
| JP | 2001128990 | 5/2001 |
| JP | 2001128990 A | 5/2001 |
| JP | 2001231870 A | 8/2001 |
| JP | 2008142467 A | 6/2008 |
| SU | 166452 | 11/1964 |
| SU | 166452 | 1/1965 |
| SU | 401367 A1 | 10/1973 |
| SU | 401367 | 11/1974 |
| SU | 727201 | 4/1980 |
| SU | 727201 A2 | 4/1980 |
| WO | 94/04220 A1 | 3/1994 |
| WO | 1994/04220 | 3/1994 |
| WO | 1996/04860 | 2/1996 |
| WO | 199604860 A1 | 2/1996 |
| WO | 97/41924 A1 | 11/1997 |
| WO | 97/43971 A2 | 11/1997 |
| WO | WO97/41924 | 11/1997 |
| WO | WO97/43971 | 11/1997 |
| WO | 97/48450 A1 | 12/1997 |
| WO | 00/13602 A2 | 3/2000 |
| WO | 2000/12010 | 3/2000 |
| WO | 2000/13602 | 3/2000 |
| WO | 0012010 A1 | 3/2000 |
| WO | 00/48672 A1 | 8/2000 |
| WO | 00/49957 A1 | 8/2000 |
| WO | 2000/49957 | 8/2000 |
| WO | WO00/48672 | 8/2000 |
| WO | 00/51513 A1 | 9/2000 |
| WO | 00/53113 A1 | 9/2000 |
| WO | 2000/053113 | 9/2000 |
| WO | WO00/51513 | 9/2000 |
| WO | 01/01847 A1 | 1/2001 |
| WO | WO01/01847 | 1/2001 |
| WO | 01/74252 A2 | 10/2001 |
| WO | WO01/74252 | 10/2001 |
| WO | 02/45790 A2 | 6/2002 |
| WO | WO02/45790 | 6/2002 |
| WO | 02/061880 A2 | 8/2002 |
| WO | WO02/061880 | 8/2002 |

(56) References Cited

FOREIGN PATENT DOCUMENTS

| WO | 04112628 A1 | 12/2004 |
|---|---|---|
| WO | WO04/112628 | 12/2004 |
| WO | 05/016119 A2 | 2/2005 |
| WO | 2005/011049 | 2/2005 |
| WO | 2005/011049 A2 | 2/2005 |
| WO | WO05/016119 | 2/2005 |
| WO | 2006/105121 | 10/2006 |
| WO | 2006/105121 A2 | 10/2006 |
| WO | 2010/035831 A1 | 4/2010 |

OTHER PUBLICATIONS

U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Anonymous. (2001) Disposable Chiba Biopsy Needles and Trays. Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division. Glens Falls, New York. (Hospital products price list), 4 pages.
Anonymous. Ground Cannulae, ISPG, New Milford, CT. (Advertisement) one page, Jul. 19, 2000.
B. Levy M.D. et al. "Update on Hysterectomy New Technologies and Techniques" OBG Management, Feb. 2003.

B. F. Mullan et al.. (May 1999) "Lung Nodules: Improved Wire for CT-Guided Localization," Radiology 211:561-565.
B. T. Heniford M.D. et al.. "Initial Research and Clinical Results with an Electrothermal Bipolar Vessel Sealer" Oct. 1999.
Bergdahl et al.. "Studies on Coagulation and the Development of an Automatic Computerized Bipolar Coagulator" Journal of Neurosurgery 75:1 (Jul. 1991), pp. 148-151.
C. H. Durney et al., "Antennas for Medical Applications", Antenna Handbook: Theory Application and Design, p. 24-40, Van Nostrand Reinhold. 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goenzel Algorithm" Aug. 1996 DOS pp. 283-297 Signal Processing, Elsevier Science Publishers B.V. Amsterdam, NL, vol. 52. No. 3.
Chou. C.K.. (1995) "Radiofrequency Hyperthermia in Cancer Therapy." Chapter 94In Biologic Effects of Nonionizing Electromagnetic Fields, CRC Press. Inc., pp. 1424-1428.
Chung et al., "Clinical Experience of Sutureless Closed Hemorrhoidectomy with LigaSure™" Diseases of the Colon & Rectum. vol. 46, No. 1, Jan. 2003.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw-Hill, vol. 111, (1984), pp. 2490-2499.
Crawford et al.. "Use of the LigaSure™ Vessel Sealing System in Urologic Cancer Surger" Grand Rounds In Urology 1999, vol. 1, Issue 4, pp. 10-17.
Esterline Product Literature, "Light Key: Visualize a Virtual Keyboard. One With No Moving Parts", 4 pages.
Herman at al., "Laparoscopic Intestinal Resection With the LigaSure™ Vessel Sealing System: A Case Report" Innovations That Work, Feb. 2002.
Johnson et al.. "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans. D.B. et al., (Nov. 1985) "Spring Hookwire Breast Lesion Localizer: Use with Rigid-Compression. Mammographic Systems," Radiology 157(2):537-538.
LigaSure™ Vessel Sealing System. the Seal of Confidence in General , Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, pp. 205-210.
McGahan et al., (1995) "Percutaneous Ultrasound-guided Radiofrequency Electrocautery Ablation of Prostate Tissue in Dogs". Acad Radiol, vol. 2, No. 1: pp. 61-65.
MDTECH product literature (Dec. 1999) "FlexStrand": product description, 1 page.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.

(56) References Cited

OTHER PUBLICATIONS

Murakami, R. et al.. (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Olsson M.D. et al.. "Radical Cystectomy in Females" Current Surgical Techniques in Urology, vol. 14, Issue 3, 2001.
P.R. Stauffer et al., "Interstitial Heating Technologies", Thermoradiotheray and Thermochemotherapy (1995) vol. I. Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan. "A Novel Technique for Parenchymal Division During Hepatectomy" The American Journal of Surgery, vol. 181, No. 3, Oapril 2001, pp. 236-237.
Reidenbach, (1995) "First Experimental Results with Special Applicators for High-Frequency Interstitial Thermotherapy". Society Minimally Invasive Therapy, 4(Suppl 1):40 (Abstr).
Rothenberg et al.. "Use of the LigaSure™ Vessel Sealing System in Minimally Invasive Surgery in Children" Int'l Pediatric Endosurgery Group (I PEG) 2000.
Sengupta et al., "Use of a Computer-Controlled Bipolar Diathermy System in Radical Preôstatectomies and Other Open Urological Surgery" ANZ Journal of Surgery (2001) 71.9 pp. 538-540.
Sugita et al., "Bipolar Coagulator with Automatic Thermocontrol" J. Neurosurg., vol. 41. Dec. 1944, pp. 777-779.
Sylvain Labonte et al., "Monopole Antennas for Microwave Catheter Ablation", IEEE Trans. on Microwave Theory and Techniques, vol. 44. No. 10, pp. 1832-1840, Oct. 1995.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite•Element Codes to Model Electrical Heating and Non•LInear Thermal Transport In Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html> last visited on Apr. 27, 2001, 3 pages.
Urrutia et al., (1988). "Retractable-Barb Needle for Breast Lesion Localization: Use in 60 Cases," Radiology 169(3):845-847.
W. Scott Helton, "LigaSure™ Vessel Sealing System: Revolutionary Hemostasis Product for General Surgery" Sales/Product Literature 1999.
European Search Report EP 03721482 dated Feb. 6, 2006.
European Search Report EP 04013772 dated Apr. 11, 2005.
European Search Report EP 04015980 dated Nov. 3, 2004.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111,dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.

(56) References Cited

OTHER PUBLICATIONS

International Search Report PCT/US99/24869 dated Feb. 11, 2000.
European Search Report 09151736.7 dated Jun. 12, 2009.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Lyndon B. Johnson Space Center, Houston, Texas, "Compact Directional Microwave Antenna for Localizing Heating," NASA Tech Briefs, Mar. 2008.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 02786604.5 dated Feb. 10, 2010.
European Search Report EP 04009964 dated Jul. 28, 2004.
European Search Report EP 04015981.6 dated Oct. 25, 2004.
European Search Report EP 04027314 dated Mar. 31, 2005.
European Search Report EP 04027479 dated Mar. 17, 2005.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.

(56) References Cited

OTHER PUBLICATIONS

U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
International Search Report PCT/US10/032796 dated Jul. 28, 2010.
Chinese Office Action (With English Translation) and Search Report, dated Sep. 28, 2015, corresponding to Chinese Application No. 201310000926.6; 13 total pages.
European Search Report dated Jul. 30, 2015, corresponding to European Application No. 15168649.0; 8 pages.
Johnson et al., "New Low-Profile Applicators for Local Heating of Tissues", IEEE Transactions on Biomedical Engineering, vol. BME-31, No. 1, Jan. 1984, pp. 28-37.
Urologix, Inc.—Medical Professionals: Targis.TM. Technology (Date Unknown). "Overcoming the Challenge" located at: <http://www.urologix.com!medicaUtechnology.html > Nov. 18, 1999; 3 pages.
Stagegaard, N., Petersen H.H., Chen X., Svendsen J.H., "Indication of the Radiofrequency Induced Lesion Size by Pre-ablation Measurements" Europace (2005) 7, 525-534.
U.S. Appl. No. 08/136,098, filed Oct. 14, 1993; Roger A. Stern.
U.S. Appl. No. 08/483,742, filed Jun. 7, 1995; Roger A. Stern.
European Examination Report from Application No. EP 03 736 458.5 dated Jul. 17, 2015.
B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.

(56) References Cited

OTHER PUBLICATIONS

Herman et al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MIDTECH product literature (Dec. 1999) "FlexStrand": product description, 1 page.
Cosman et al., "Methods of Making Nervous System Lesions" in William RH, Rengachary SS (eds): Neurosurgery, New York: McGraw.cndot.Hill, vol. 111, (1984), pp. 2490-2499.
Johnson, "Evaluation of the LigaSure.TM. Vessel Sealing System in Hemorrhoidectormy" American College of Surgeons (ACS) Clinic La Congress Poster (2000).
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 08300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.

* cited by examiner

MICROWAVE ABLATION DEVICES INCLUDING EXPANDABLE ANTENNAS AND METHODS OF USE

CROSS-REFERENCE TO RELATED APPLICATIONS

This application claims the benefit of priority to U.S. Provisional Application Ser. No. 61/039,851 entitled "MICROWAVE ABLATION DEVICES INCLUDING EXPANDABLE ANTENNAS AND METHODS OF USE" filed Mar. 27, 2008 by Chris Rusin et al, which is incorporated by reference herein.

BACKGROUND

Technical Field

The present disclosure relates to microwave ablation devices and methods. More particularly, the disclosure relates to microwave antennas that are insertable into tissue and capable of being expanded.

Background of Related Art

In the treatment of diseases such as cancer, certain types of cancer cells have been found to denature at elevated temperatures that are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great amount of control. This is partly why a more direct and precise method of applying microwave radiation has been sought.

Presently, there are several types of microwave probes in use, e.g., monopole, dipole, and helical. One type is a monopole antenna probe consisting of a single, elongated microwave conductor exposed at the end of the probe. The probe is sometimes surrounded by a dielectric sleeve. The second type of microwave probe commonly used is a dipole antenna consisting of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

Because of the perpendicular pattern of microwave energy radiation, conventional antenna probes are typically designed to be inserted directly into the tissue, e.g., a tumor, to be radiated. However, such typical antenna probes commonly fail to provide uniform heating axially and/or radially about the effective length of the probe.

It is often difficult to assess the extent to which the microwave energy will radiate into the surrounding tissue, i.e., it is difficult to determine the area or volume of surrounding tissue that will be ablated. Furthermore, when conventional microwave antennas are inserted directly into the tissue, e.g., cancerous tissue, there is a danger of dragging or pulling cancerous cells along the antenna body into other parts of the body during insertion, placement, or removal of the antenna probe.

One conventional method for inserting and/or localizing wires or guides includes a wire guide that is delivered into breast tissue, for example, through a tubular introducer needle. When deployed, the wire guide cuts into and scribes a circular path about the tissue distal to a lesion while the remainder of the distal portion of the wire guide follows the path scribed by the distal tip and locks about the tissue.

In certain circumstances, it is advantageous to create a relatively large ablation region, which often requires multiple ablation instruments to be inserted into a patient. It would therefore be desirable to provide a single instrument that can be used to create a relatively large ablation region.

SUMMARY

A microwave ablation device for treating tissue includes an inner conductor having a length and a distal end and configured to deliver energy, a wire extending adjacent the inner conductor and axially translatable relative thereto, the wire including a length and a distal end, a distal tip disposed in mechanical cooperation with the distal end of the inner conductor and the distal end of the wire; and an outer conductor including a distal end and defining a longitudinal axis, the outer conductor at least partially surrounding the inner conductor and the wire at least partially along their lengths. The distal tip is movable substantially along the longitudinal axis with respect to the outer conductor and relative movement of the distal tip towards the distal end of the outer conductor causes at least a portion of the inner conductor to move away from the longitudinal axis.

The inner conductor may arc away from the longitudinal axis in response to the relative movement of the distal tip with respect to the distal end of the outer conductor, and at least a portion of the inner conductor may be flexible. Also, at least a portion of the inner conductor may be configured to pierce tissue.

A corner may be formed on the inner conductor in response to movement of the distal tip with respect to the distal end of the outer conductor, and this corner may be uninsulated.

In some embodiments, the microwave ablation device may further include at least a second inner conductor, the second inner conductor including a length and a distal end and connected to the distal tip adjacent the distal end thereof.

In some embodiments, the distal tip is configured to pierce tissue and is electrically coupled to the distal end of the inner conductor.

In some embodiments, relative movement of the distal tip away from the distal end of the outer conductor causes at least a portion of the inner conductor to move towards the longitudinal axis.

In some embodiments, a dielectric material may be disposed between the outer conductor and the inner conductor.

In some embodiments, the inner conductor is an expandable mesh.

DESCRIPTION OF THE DRAWINGS

Embodiments of the presently disclosed microwave ablation devices are disclosed herein with reference to the drawings, wherein.

DETAILED DESCRIPTION OF EMBODIMENTS

Figure 1:
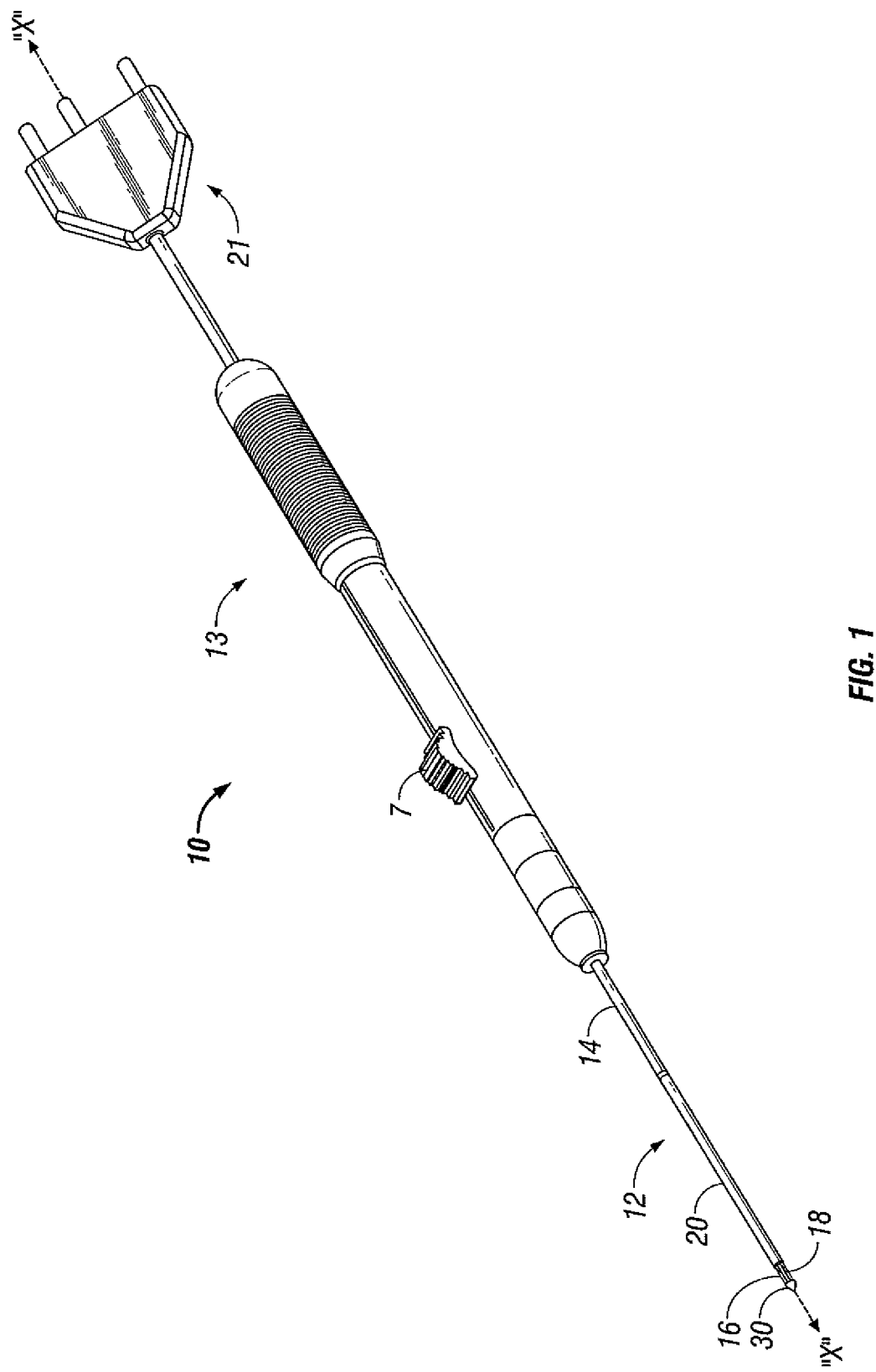
FIG. 1 is a perspective view of a microwave ablation device in accordance with an embodiment of the present disclosure.

Embodiments of the presently disclosed microwave ablation devices are described in detail with reference to the drawings, in which like reference numerals designate identical or corresponding elements in each of the several views. As used herein the term "distal" refers to that portion of the microwave ablation device, or component thereof, farther from the user while the term "proximal" refers to that portion of the microwave ablation device or component thereof, closer to the user.

An ablation device (e.g., a microwave ablation device) in accordance with the present disclosure is referred to in the figures as reference numeral 10. Referring initially to FIG. 1, microwave ablation device 10 includes a microwave antenna 12 and a handle portion 13. Microwave antenna 12 includes a shaft or feedline 14 having at least one inner conductor 16, a wire 18 and an outer structure 20, which defines a longitudinal axis X-X. A power transmission cord 21 is shown to connect microwave ablation device 10 to a suitable electrosurgical generator 23 (see FIG. 2). Additionally, an actuation element 7 is illustrated in FIG. 1 in accordance with various embodiments of the present disclosure.

Figure 2:
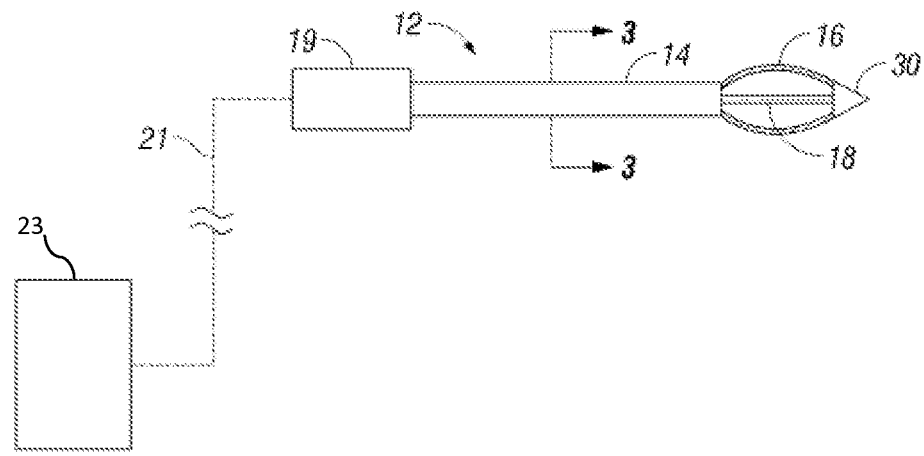
FIG. 2 is a schematic view of the microwave ablation device of FIG. 1 connected to a generator.

As seen in FIG. 2, each inner conductor 16 extends from feedline 14 and a penetrating tip 30 is disposed adjacent to or coupled to a distal end of each inner conductor 16. In the illustrated embodiment, the proximal end of feedline 14 includes a coupler 19 that electrically couples antenna 12 to generator 23 via power transmission cord 21.

It is envisioned that microwave ablation device 10 may be introduced to the treatment site via a straight, arcuate, non-deployable and/or deployable applicator or introducer. It is further envisioned that tip 30 is configured to pierce tissue to facilitate introduction of microwave ablation device 10 to the treatment site.

As described above and as shown in FIG. 3, feedline 14 may be in the form of a coaxial cable. Portions of feedline 14 may be formed of an outer structure 20 (e.g., an outer conductor) surrounding at least one inner conductor 16. Each inner conductor 16 and/or outer structure 20 may be made of a suitable conductive metal that may be semi-rigid or flexible, such as, for example, copper, gold, or other conductive metals with similar conductivity values. Alternatively, portions of each inner conductor 16 and outer structure 20 may also be made from stainless steel that may additionally be plated with other materials, e.g., other conductive materials, to improve their properties, e.g., to improve conductivity or decrease energy loss, etc.

For example, inner conductors 16 may be made of stainless steel having an impedance of about 50Ω. In order to improve a conductivity of a stainless steel inner conductor 16, inner conductor 16 may be coated with a layer of a conductive material such as copper or gold. Although stainless steel may not offer the same conductivity as other metals, it does offer increased strength required to puncture tissue and/or skin.

Figure 3:
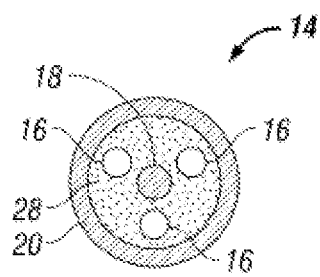
FIG. 3 is a cross-sectional view of a portion of a feedline of the microwave ablation device of FIGS. 1 and 2, as taken through 3-3 of FIG. 2.

With continued reference to FIG. 3, feedline 14 of antenna 12 is shown including a dielectric material 28 surrounding at least a portion of a length of each inner conductor 16 and outer structure 20 surrounding at least a portion of a length of dielectric material 28 and/or each inner conductor 16. That is, a dielectric material 28 is interposed between inner conductor 16 and outer structure 20, to provide insulation therebetween and may be comprised of any suitable dielectric material.

Various embodiments of a distal portion 22 of microwave ablation device 10 are shown in FIGS. 4-12. With specific reference to FIGS. 4 and 5, distal portion 22 of microwave ablation device 10 includes at least one inner conductor 16 (e.g., three inner conductors 16a, 16b and 16c being shown in FIG. 5), a wire 18, an outer structure or conductor 20 and a distal tip 30. Distal tip 30 is in mechanical cooperation with each inner conductor 16 and wire 18 and is movable with respect to outer structure or conductor 20. In some embodiments, distal tip 30 is also in electrical communication with each inner conductor 16 and wire 18.

It is envisioned that translation of actuation element 7 (see FIG. 1) causes movement of distal tip 30 (substantially along longitudinal axis X-X) with respect to outer structure or conductor 20. Moreover, distal translation of actuation element 7 causes distal tip 30 to move distally in the direction of arrow "A" and proximal translation of actuation element 7 causes distal tip 30 to move proximally in the direction of arrow "B." It is also contemplated that distal translation of actuation element 7 may cause outer structure 20 to move distally in the direction of arrow B and proximal translation of actuation element 7 may cause outer structure 20 to move proximally in the direction of arrow A.

Figure 4:
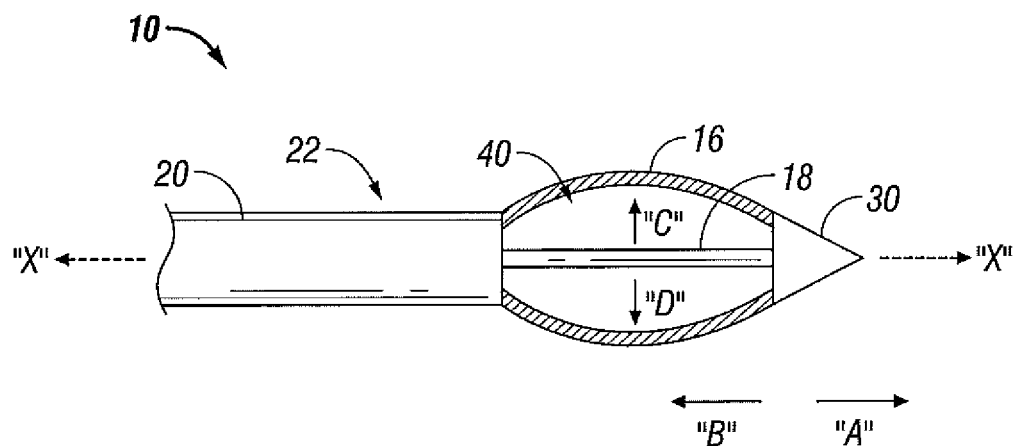
FIG. 4 is a side view of a distal portion of the microwave ablation device of FIG. 1-3.
Figure 5:
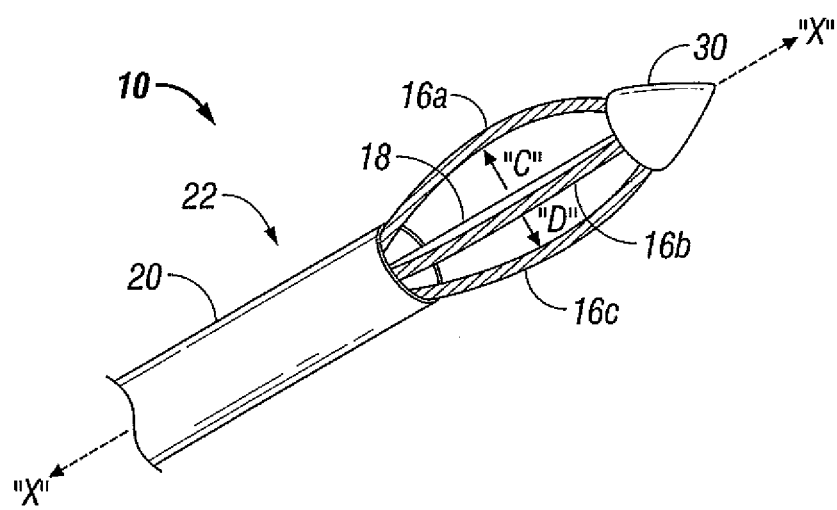
FIG. 5 is a perspective view of the distal portion of the microwave ablation device of FIGS. 1-4.

In response to the relative movement between outer structure or conductor 20 and distal tip 30, at least a portion of each inner conductor 16 is forced radially away from longitudinal axis X-X, in the direction of arrows "C" and/or "D" (see FIG. 5). Thus, an ablation region 40, as defined by the boundaries of inner conductors 16a, 16b, 16c (including the area between inner conductors 16a, 16b, 16c and adjacent wire 18), is expanded (e.g., widened) as a distance between outer structure or conductor 20 and distal tip 30 becomes smaller. In the embodiment illustrated in FIGS. 4 and 5, inner conductors 16a, 16b, 16c arc away from longitudinal axis X-X. In such an embodiment, it is envisioned that at least a portion of each inner conductor 16 is flexible.

Each inner conductor 16 may be configured to pierce or slice through tissue, either mechanically and/or with the aid of energy, e.g., radiofrequency energy. In the embodiment where inner conductor(s) 16 can mechanically pierce or slice through tissue, inner conductors) 16 may be thin enough to pierce or slice through tissue upon the exertion of a predetermined amount of force (e.g., the amount of force created when outer structure or conductor 20 and distal tip 30 are approximated). Additionally or alternatively, inner conductor(s) 16 may be configured to receive energy, e.g., from a generator, to piece or slice through tissue or assist in piercing or slicing through tissue.

Figure 6:
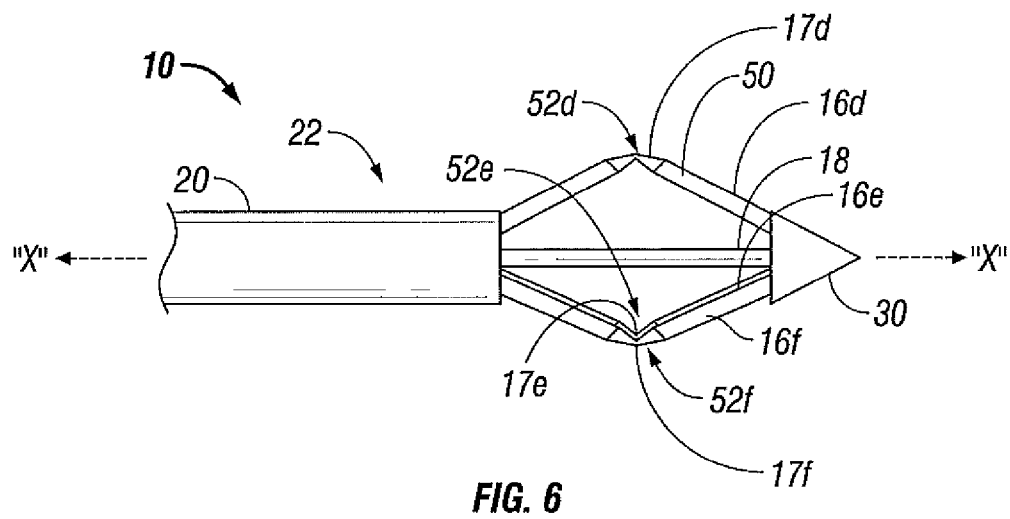
FIG. 6 is a side view of a distal portion of the microwave ablation device of FIG. 1 in a first stage of deployment, in accordance with an embodiment of the present disclosure.
Figure 7:
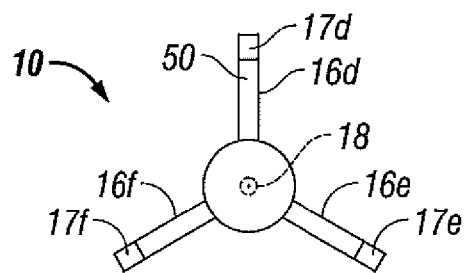
FIG. 7 is a distal end view of the distal portion of the microwave ablation device of FIGS. 1 and 6.
Figure 8:
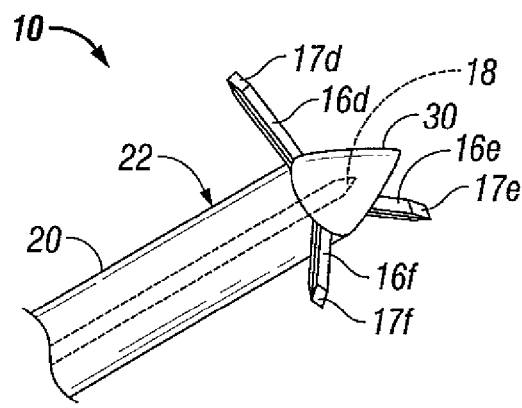
FIG. 8 is a perspective view of the distal portion of the microwave ablation device of FIGS. 1, 6 and 7 in a second stage of deployment.

Another embodiment of microwave ablation device 10 is illustrated in FIGS. 6-8. Here, upon decreasing the distance between outer structure 20 and distal tip 30, inner conductors 16d, 16e, 16f move away from longitudinal axis X-X, such that each inner conductor 16d, 16e, 16f forms a corner, point or bend 17d, 17e, 17f, respectively (as opposed to forming an arc-like shape as shown in FIGS. 4 and 5).

It is envisioned that insulation 50 may be disposed on at least a portion of inner conductors 16 of the various embodiments disclosed herein. For example, as seen in FIGS. 6-8, inner conductors 16d, 16e, 16f include insulation 50 along at least a portion of their lengths and define a respective uninsulated or exposed portion 52d, 52e, 52f (e.g., adjacent and/or including bends 17d, 17e, 17f).

Figure 9:
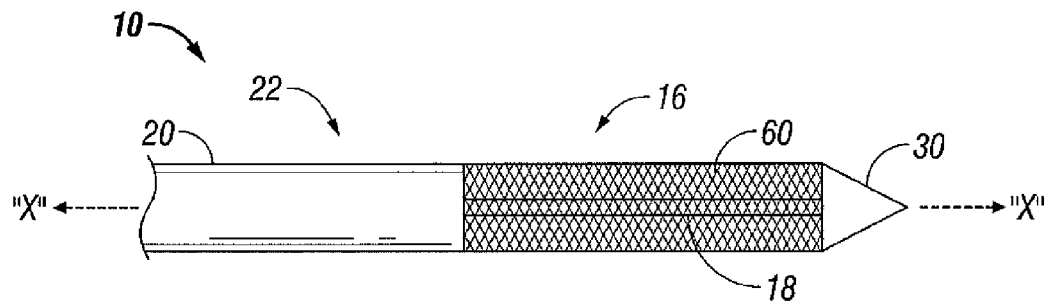
FIGS. 9 and 10 are sides views of a distal portion of a microwave ablation device in accordance with another embodiment of the present disclosure illustrating various stages of deployment thereof.
Figure 10:
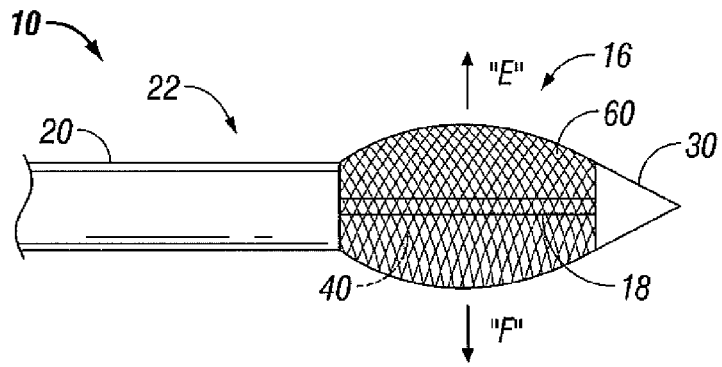

In the embodiment illustrated in FIGS. 9 and 10, inner conductor 16 is in the form of an expandable mesh 60. Here, expandable mesh 60 extends between outer structure or conductor 20 and distal tip 30 and defines ablation region 40 therebetween. Upon relative movement of distal tip 30 and outer structure or conductor 20, at least a portion of expandable mesh 60 moves or deflects away from wire 18 (as shown by arrows "E" and "F" in FIG. 10). Expandable mesh 60 may be configured to deliver energy, e.g., radiofrequency, ultrasound, cryotherapy energy, laser energy and/or microwave energy to the target tissue.

Figure 11:
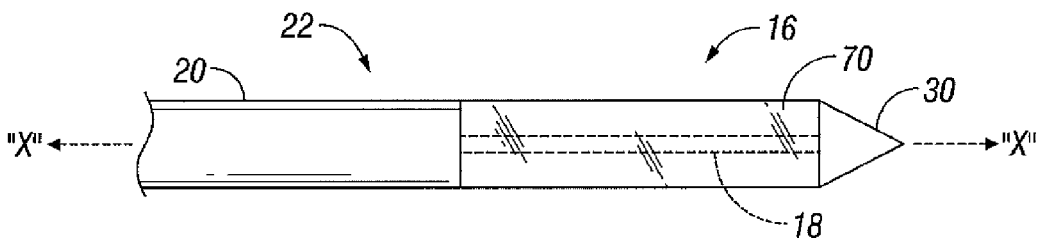
FIGS. 11 and 12 are sides views of a distal portion of a microwave ablation device in accordance with another embodiment of the present disclosure illustrating various stages of deployment thereof.
Figure 12:
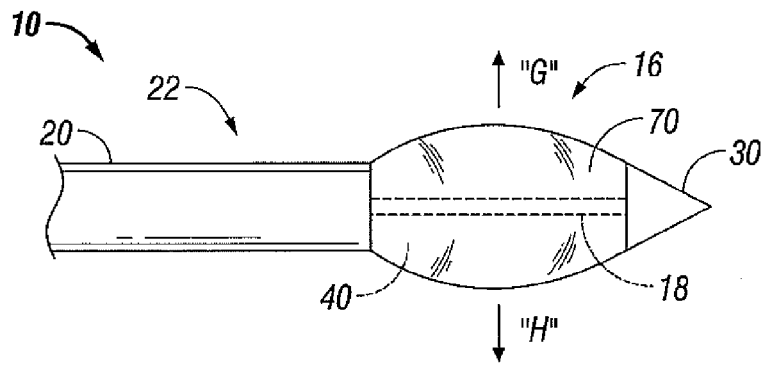

In the embodiment illustrated in FIGS. 11 and 12, inner conductor 16 is in the form of an expandable sheath 70. In this embodiment, expandable sheath 70 (e.g., including a polymeric material) is used to create or define ablation region 40. Expandable sheath 70 may be filled or inflated with a conductive material, a dielectric material or a combination thereof. Upon relative movement between distal tip 30 and outer structure 20, at least a portion of expandable sheath 70 moves away from wire 18 (as shown by arrows "G" and "H" in FIG. 12). Expandable sheath 70 may be configured to deliver energy, e.g., radiofrequency, ultrasound, cryotherapy energy, laser energy and/or microwave energy.

A method of treating tissue using ablation device 10 is also included by the present disclosure. The method may include at least providing an microwave ablation device, such as ablation device 10 described above, inserting at least a portion of the ablation device into a target surgical site while in a collapsed condition, moving a distal tip of the ablation device to cause at least a portion of an inner conductor to move away from a longitudinal axis thereof, and delivering energy to the target surgical site via at least a portion of the inner conductor. The method may further include moving a distal tip of the ablation device to cause at least a portion of an inner conductor to move towards the longitudinal axis thereof, and withdrawing the ablation device from the target surgical site. The method may further include energizing at least a portion of the ablation device during insertion of the portion of the ablation device into the target surgical site.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

The invention claimed is:

1. A microwave ablation device for treating tissue, comprising:
   a feedline including an outer conductor defining a longitudinal axis and an inner conductor coaxially disposed within the outer conductor, the outer and inner conductors conducting microwave energy for treating tissue;
   an expandable sheath formed by the inner conductor, the expandable sheath extending beyond a distal end of the outer conductor and configured to deliver microwave energy to tissue, a portion of the expandable sheath configured to move between an expanded configuration and a non-expanded configuration;
   a wire disposed coaxially within the outer conductor and extending through the expandable sheath, the wire axially translatable relative to the outer conductor;
   a distal tip physically and electrically coupled to a distal end portion of the expandable sheath and a distal end portion of the wire, wherein the portion of the expandable sheath moves towards the expanded configuration upon proximal movement of the distal tip with respect to the outer conductor; and
   a dielectric material disposed between the outer conductor and the inner conductor and surrounding at least a portion of the wire.

2. The microwave ablation device according to claim 1, wherein at least a portion of the expandable sheath arcs away from the longitudinal axis in response to movement of the distal tip towards the distal end of the outer conductor.

3. The microwave ablation device according to claim 1, wherein at least a portion of the expandable sheath is flexible.

4. The microwave ablation device according to claim 1, wherein the expandable sheath is filled or inflated with a combination of conductive and dielectric materials.

5. The microwave ablation device according to claim 1, wherein the distal tip extends between a distal end configured to pierce tissue and a proximal end directly coupled to a distal end of the wire.

6. The microwave ablation device according to claim 1, wherein movement of the distal tip away from the distal end of the outer conductor causes at least a portion of the expandable sheath to move towards the longitudinal axis.

7. The microwave ablation device according to claim 1, wherein proximal movement of the wire causes at least a portion of the expandable sheath to move away from the longitudinal axis.

8. A method of treating tissue, comprising:
   providing a microwave ablation device, including:
      a feedline including an outer conductor including a distal end and defining a longitudinal axis and an inner conductor coaxially disposed within the outer conductor, the outer and inner conductors conducting microwave energy for treating tissue;
      an expandable sheath formed by the inner conductor, the expandable sheath extending from the distal end of the outer conductor and configured to deliver microwave energy to tissue, the expandable sheath including a distal end;
      a distal tip electrically coupled to the distal end of the expandable sheath; and
      a dielectric material disposed between the outer conductor and the inner conductor;

inserting at least a portion of the microwave ablation device into tissue with at least a portion of the expandable sheath in a non-expanded configuration;

deploying at least a portion of the expandable sheath radially away from the longitudinal axis towards an expanded configuration upon movement of the distal tip towards the distal end of the outer conductor; and delivering microwave energy through at least a portion of the expandable sheath to tissue.

9. The method of claim 8, further comprising moving the distal tip away from the distal end of the outer conductor causing at least a portion of the expandable sheath to move towards the longitudinal axis.

10. The method of claim 8, further comprising withdrawing at least a portion of the microwave ablation device from the tissue.

11. The method of claim 8, further comprising delivering microwave energy to tissue as at least a portion of the microwave ablation device is deployed.

12. An electrosurgical system for treating tissue, the system including:

an electrosurgical generator; and a microwave ablation device, including:

a feedline including an outer conductor including a distal end and defining a longitudinal axis and an inner conductor coaxially disposed within the outer conductor, the outer and inner conductors conducting microwave energy for treating tissue;

an expandable sheath formed by the inner conductor, the expandable sheath extending from the distal end of the outer conductor and configured to deliver microwave energy to tissue, the expandable sheath including a distal end and a length, the expandable sheath configured to move between an expanded configuration and a non-expanded configuration;

a wire disposed coaxially within the outer conductor and extending through the extendable sheath, the wire axially translatable relative to the outer conductor;

a distal tip coupled to the distal end of the expandable sheath and a distal end of the wire, the distal tip electrically coupled to the expandable sheath and the wire, wherein at least a portion of the expandable sheath moves radially away from the longitudinal axis towards the expanded configuration upon movement of the distal tip with respect to the outer conductor; and a dielectric material disposed between the outer conductor and the inner conductor and surrounding at least a portion of the wire.

13. The electrosurgical system according to claim 12, wherein at least a portion of the expandable sheath is filled or inflated with a combination of conductive and dielectric materials.

14. The electrosurgical system according to claim 12, wherein movement of the distal tip away from the distal end of the outer conductor causes at least a portion of the expandable sheath to move towards the longitudinal axis.

* * * * *